United States Patent
Elhawary et al.

(10) Patent No.: US 10,687,911 B2
(45) Date of Patent: Jun. 23, 2020

(54) POSITIONING AND ORIENTATION OF SURGICAL TOOLS DURING PATIENT SPECIFIC PORT PLACEMENT

(71) Applicant: KONINKLIJKE PHILIPS N.V., Eindhoven (NL)

(72) Inventors: Haytham Elhawary, New York, NY (US); Aleksandra Popovic, New York, NY (US); Raymond Chan, San Diego, CA (US); Robert Manzke, Bonebuttel (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1347 days.

(21) Appl. No.: 14/362,225

(22) PCT Filed: Nov. 23, 2012

(86) PCT No.: PCT/IB2012/056687
§ 371 (c)(1),
(2) Date: Jun. 2, 2014

(87) PCT Pub. No.: WO2013/084107
PCT Pub. Date: Jun. 13, 2013

(65) Prior Publication Data
US 2014/0350572 A1    Nov. 27, 2014

Related U.S. Application Data

(60) Provisional application No. 61/566,762, filed on Dec. 5, 2011.

(51) Int. Cl.
*A61B 34/30* (2016.01)
*A61B 90/10* (2016.01)
*A61B 90/11* (2016.01)

(52) U.S. Cl.
CPC .............. *A61B 90/11* (2016.02); *A61B 34/30* (2016.02); *A61B 2034/304* (2016.02); *A61B 2090/103* (2016.02)

(58) Field of Classification Search
CPC ......... A61B 34/30; A61B 90/30; A61B 90/13; A61B 2090/103; A61B 90/11; A61B 19/201; A61B 2034/304; A61B 2034/107
(Continued)

(56) References Cited

U.S. PATENT DOCUMENTS 5,638,819 A    6/1997   Manwaring et al.
6,558,318 B1   5/2003   Daniel et al.
(Continued)

FOREIGN PATENT DOCUMENTS

DE    102009012987    2/2010
JP    2010528763 A    8/2010
(Continued)

*Primary Examiner* — Katrina M Stransky (57) ABSTRACT

A positioning apparatus includes a first portion (123) having a first opening (125) for alignment with a port entry point. A second portion (127) is positionable for alignment with the first opening from a plurality of different positions. An actuation mechanism (142) is coupled to at least one of the first portion and the second portion to set relative positions of the first and second portions to permit a tool axis formed between the first and second portions to be aligned through the first opening such that a tool (104) provided on the tool axis would include a known position and orientation.

19 Claims, 8 Drawing Sheets

(58) Field of Classification Search
USPC .......................................................... 606/130
See application file for complete search history.

(56) References Cited

U.S. PATENT DOCUMENTS

| | | | |
|---|---|---|---|
| 7,927,271 | B2 | 4/2011 | Dimitriou et al. |
| 8,747,418 | B2 | 6/2014 | Qiresjo et al. |
| 2002/0156369 | A1 | 10/2002 | Chakeres |
| 2004/0122446 | A1 | 6/2004 | Solar |
| 2006/0189842 | A1 | 8/2006 | Hoeg et al. |
| 2006/0229641 | A1 | 10/2006 | Gupta et al. |
| 2008/0200798 | A1 | 8/2008 | Eklund et al. |
| 2008/0312499 | A1* | 12/2008 | Handa ................. A61B 1/0005 600/109 |
| 2009/0112082 | A1 | 4/2009 | Keidl et al. |
| 2009/0113082 | A1 | 4/2009 | Adar et al. |
| 2009/0171184 | A1* | 7/2009 | Jenkins ............... A61B 5/7435 600/411 |
| 2010/0160771 | A1 | 6/2010 | Gielen et al. |
| 2011/0251624 | A1* | 10/2011 | Yi ..................... A61B 17/3403 606/130 |

FOREIGN PATENT DOCUMENTS

| | | |
|---|---|---|
| WO | WO2006048097 | 5/2006 |
| WO | WO2006081409 | 8/2006 |
| WO | WO2010017641 | 2/2010 |

\* cited by examiner

POSITIONING AND ORIENTATION OF SURGICAL TOOLS DURING PATIENT SPECIFIC PORT PLACEMENT

CROSS-REFERENCE TO PRIOR APPLICATIONS

This application is the U.S. National Phase application under 35 U.S.C. § 371 of International Application Serial No. PCT/IB2012/056687, filed on Nov. 23, 2012, which claims the benefit of U.S. Application Ser. No. 61/566,762, filed on Dec. 5, 2011. These applications are hereby incorporated by reference herein.

This disclosure relates to medical instruments and more particularly to devices, systems and methods for use in medical applications for improving alignment with patient-specific port placement.

Minimally invasive surgery is performed using elongated instruments inserted into a patient's body through small ports. Placement of ports plays an important role in the outcome of the surgery. Standard clinical guidelines define entry points with respect to well-known anatomical landmarks. For example, in cardiac surgery, the ribs, sternum, and nipple, and defined distances from these features are employed. This kind of guidance does not account for anatomical variation due to patient size or pathology present. In port planning based on pre-procedural datasets, there remains a gap in clinical implementation due to the challenge of executing plans during live cases.

Figure 1:
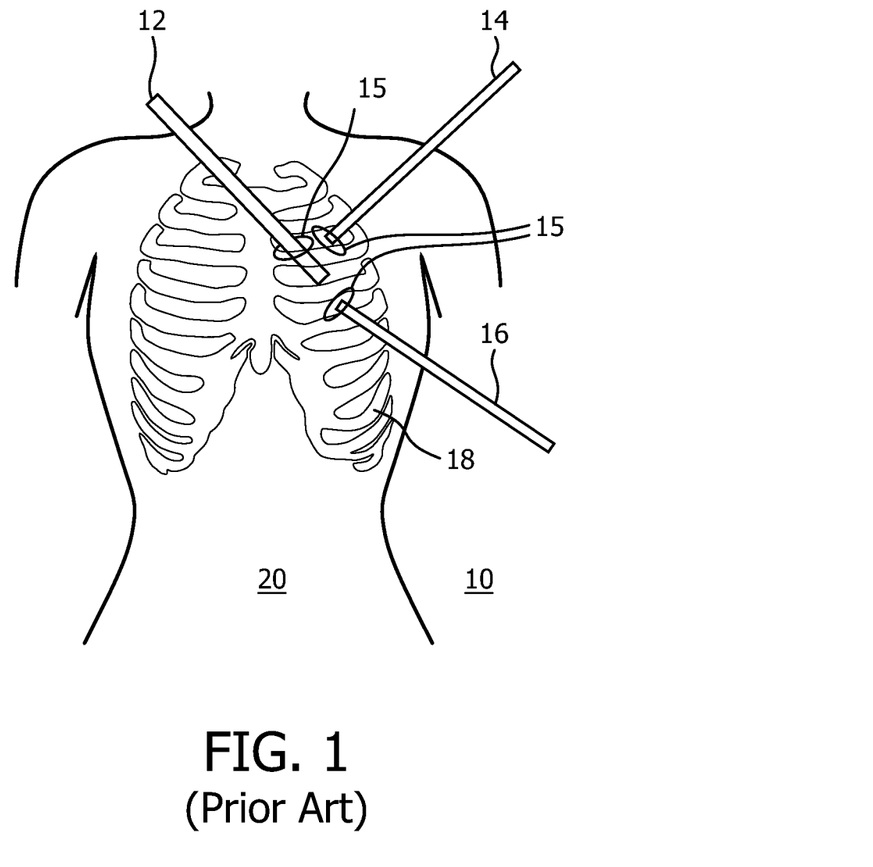
FIG. 1 is a diagram showing a setup for a minimally invasive cardiac surgery in accordance with the prior art.

Referring to FIG. 1, a setup 10 for a minimally invasive cardiac surgery is illustratively shown. In this example, an endoscope 12 and two instruments 14 and 16 are inserted through ribs 18 into a body cavity 20 through small ports 15, which may include a size of between about 5 mm and about 100 mm. In clinical practice, the ports 15 are selected using guidelines published by professional associations, hospitals, or manufacturers of surgical equipment. The guidelines define entry points with respect to anatomical landmarks, for example, ribs, sternum, nipple, distances between and from these features, etc. Generally, however, this kind of guidance does not include variability in anatomy, patient size, specificity of patient's disease, etc. Therefore, a more patient-specific port placement may be beneficial, which minimizes access-related tissue trauma and procedure times while improving outcomes.

Patient specific port planning facilitates interventions, potentially reducing procedure times and complication rates while improving outcomes. In a standard clinical practice, surgical access ports are selected using the standard guidelines. The lack of patient-specific optimization can have the result that instruments positioned in a suboptimal port may not be able to reach all areas of interest. This in turn prolongs intervention time and increases the amount of surgery performed to reach target sites. Intra-procedural execution of patient specific access port optimization remains unresolved.

After the instruments, e.g., 12, 14 and 16 are inserted into the body cavity 20, the instruments 12, 14 and 16 can be moved with four degrees-of-freedom (DOF)—two angles pivoting around the port 15 (fulcrum point) in addition to insertion and rotation. Whereas rotation and insertion are intuitive and easy to use, mapping between the angles and endoscope view is less intuitive, takes a long time to learn and, as studies show, is the largest difficulty in hand-eye coordination in minimally-invasive surgery.

Much focus has been placed on solving the port placement problem. Computer algorithms have been developed to compute optimal ports for instruments based on preoperative three-dimensional medical images (e.g., computed tomography (CT) scans, magnetic resonance imaging (MRI), etc.). Subsequent translation of optimal plans into an operating room has focused on using standard tool tracking technologies known from surgical navigation. However, there remains a gap in clinical implementation due to the non-intuitive nature of instrument manipulation under endoscopic guidance. Methods proposed in the prior art based on port placement optimization with pre-procedural imaging and conventional tracking technology (e.g., near-infrared optical camera based localization, computer vision based localization, electromagnetic localization) are not sufficiently practical for use in standard clinical practice.

Port placement optimization performed prior to surgery based on preoperative 3D imaging may be outdated once the surgery starts. For example, in cardiac surgery, the left lung is deflated and the heart may be stopped using a heart-lung pump, causing different arrangements of organs. Also, the ports are planned with respect to preoperative images and not relative to an endoscope video despite the fact that endoscopy is the only real-time visual feedback available to an interventionalist. Realistic patient-specific port planning requires significant overhead in time and is indicative of the limited clinical application of surgical simulation tools to date. Also, conventional tracking systems usually incur long set-up times in the operating room and require careful calibration. For cases in which tracking is not used during later stages of surgery, the clinical overhead required for preparation may not be acceptable. While port placement locations define and constrain the insertion points for interventional instruments and endoscopy probes, there is still a need for intuitive feedback with regard to how the tools should be oriented to reach specific areas in the endoscopy images, which is lacking in procedures today. Therefore, there is a need for improved localization and manipulation of instruments in interventional procedures.

In accordance with the present principles, a positioning apparatus includes a first portion having a first opening for alignment with a port entry point. A second portion is positionable for alignment with the first opening from a plurality of different positions. An actuation mechanism is coupled to at least one of the first portion and the second portion to set relative positions of the first and second portions to permit a tool axis formed between the first and second portions to be aligned through the first opening such that a tool provided on the tool axis would include a known position and orientation.

Another positioning apparatus includes a first plate having a first opening for alignment with a port entry point, and a second plate having a second opening for alignment with the first opening. An actuation mechanism is coupled to at least one of the first plate and the second plate and set to permit a tool axis to be aligned through the first and second openings such that a tool provided on the tool axis would pass through the port entry point with a known position and orientation.

Yet another positioning apparatus includes a first slotted arch hingedly coupled to a base, and a second slotted arch hingedly coupled to the base and disposed orthogonally with respect to the first slotted arch. A channel passes through a slot in the first slotted arch and a slot of the second slotted arch for alignment of the channel with a center of rotation corresponding with a port entry point such that rotation of the tool axis is controlled by rotations of the first and second slotted arches to provide alignment for a known position and orientation of the tool axis.

A method for positioning instruments includes placing a scope in a first port in a subject; determining a position for a second port for an instrument; mounting a positioning and orientation apparatus to the subject, the positioning and orientation apparatus including at least two openings with adjustable positions for aligning a tool axis with respect to the second port; and positioning a tool along the tool axis through the at least two openings in accordance with a field of view of the scope.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

In accordance with the present principles, arrangements for positioning and orientation of a surgical tool with respect to an endoscopic device, imaging device or other instrument are provided. Patient specific port planning requires knowledge and control of the interventional instrument relative to the endoscope, in addition to visualization of the surgical tool position and path superimposed on the endoscopic view. The patient specific port plan can also be performed with knowledge and control of the interventional instrument relative to an external patient registered tracking device, including but not limited to electromagnetic tracking methods, optical-based tracking methods, camera-based tracking methods, optical shape sensing etc., or to an intra-operative imaging device.

It should be understood that the present invention will be described in terms of medical instruments; however, the teachings of the present invention are much broader and are applicable to any instruments. In some embodiments, the present principles are employed in tracking or analyzing complex biological or mechanical systems. In particular, the present principles are applicable to internal procedures with respect to biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 2:
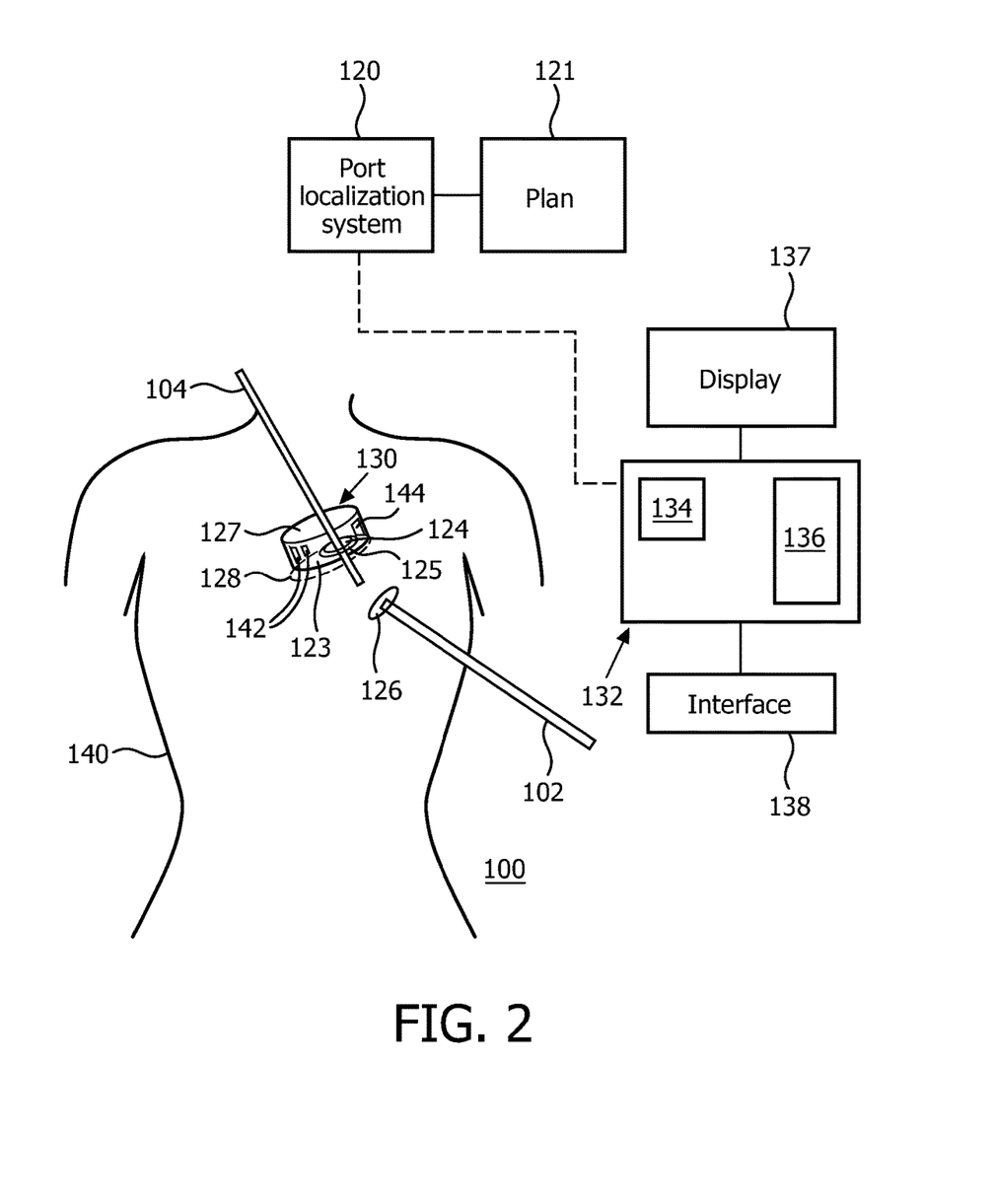
FIG. 2 is a diagram showing a setup for a minimally invasive cardiac surgery employing a positioning and orientation apparatus in accordance with the present principles.

Referring now to the drawings in which like numerals represent the same or similar elements and initially to FIG. 2, a setup 100 for a minimally invasive cardiac surgery is illustratively shown in accordance with one embodiment. In this example, an endoscopically guided surgery includes the use of a real-time port localization system 120 with software and hardware that permit for planning, prediction, and measurement of a position of a surgical tool relative to an endoscopic image or data stream. The port localization system 120 is shown separate from a computer 132, but may be included or employed with the computer 132. The port localization system 120 may employ known methods of locating a port position(s) 124, 126 and therefore a position and orientation of a surgical tool such as an endoscope 102 or other tools 104. In accordance with the present principles, a position and orientation apparatus 130 (shown generically) is attached in a calibrated fashion to the tool 104 (or to endoscope 102) to permit real-time manipulation of the surgical tool 104 (or endoscope 102) relative to a live endoscopy data stream or other external tracking or intra-operative imaging method. The device or apparatus 130 such as this permits the positioning of the surgical tool 104 (or endoscope 102) in such a manner so as to localize the surgical tool 104 (or endoscope 102) in a region selected by a surgeon on an endoscope image. A mounting position or mechanism 128 is indicated or placed on the subject 140 to identify a position for or to secure the apparatus 130.

The positioning apparatus 130 includes a first portion 123 having a first opening 125 for alignment with the port entry point 124. A second portion 127 has a guide for alignment with the first opening 125. An actuation mechanism 142 is coupled to at least one of the first portion 123 and/or the second portion 127 and set to permit a tool axis to be aligned through the first opening 125 such that a tool 104 provided on the tool axis would pass through to a patient specific location in accordance with a plan 121. The plan 121 may be created and stored using software and patient specific data acquired through medical images, measurements or the like.

By providing a positioning apparatus 130, a more reliable location of a medical instrument can be realized within a field of view of a scope or camera. In this way, patient-specific adjustments may be consistently and repeatedly made in real-time, improving instrument placement and overall success of an interventional procedure. Exemplary embodiments for the tool positioning and orienting arrangement/apparatus 130 will be described in greater detail below.

Figure 3:
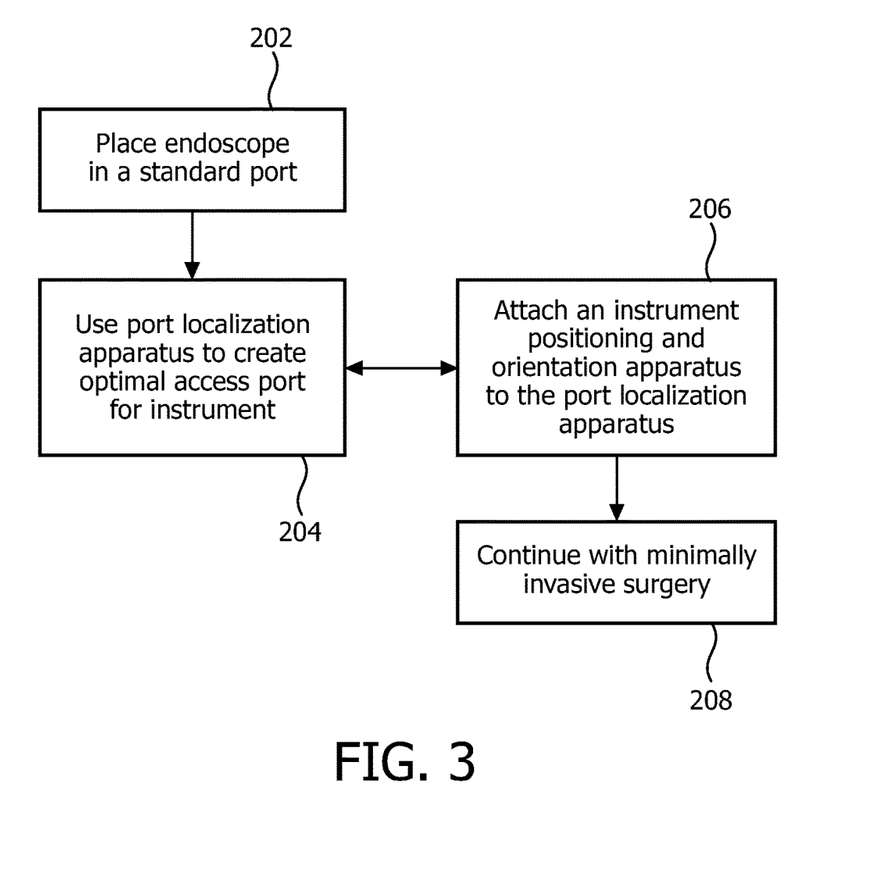
FIG. 3 is a flow diagram showing clinical workflow in accordance with one embodiment.

Referring to FIG. 3 with continued reference to FIG. 2, a clinical workflow is illustratively shown in accordance with one embodiment. In block 202, the workflow begins with an endoscope insertion within a standard port. In block 204, a port localization system 120 is employed to identify and create an optimal access port for the interventional instrument. In block 206, a positioning and orientation apparatus 130 in accordance with the present principles is employed either before or after optimal port creation for attachment and manipulation of the surgical instrument at the optimal access location. In block 208, the surgical procedure then proceeds or continues following tool deployment within the body with live feedback about one or more of: interventional tool location, tool orientation, pathway information (predicted and/or actual), in addition to any other auxiliary information from physiological monitoring or pre-procedural information. The data may be overlaid on the endoscopy data stream images.

During surgery, interventional tools assume different orientations. Therefore, it is beneficial to provide a surgeon with the ability to plan and manipulate the position/orientation of a tool with respect to many potential orientations. The surgeon is also enabled to plan and manipulate the position/orientation of an instrument once the ports are selected, to simplify hand-eye coordination tasks.

Referring again to FIG. 2, manipulation of apparatus 130 in the embodiments below can be performed manually, semi-automatically or automatically. The computer system 132 having a processor 134, memory 136, a display 137 and a user interface 138 may be employed to control movement of the apparatus 130, assist in localization or placement of the apparatus 130 relative to a port location or anatomical landmarks, be employed for developing a plan or otherwise provide guidance to a user. These embodiments are preferably combined with optimal port localization arrangements to facilitate minimally-invasive endoscope guided procedures.

The apparatus 130 may include (semi)automated electro-mechanical, electro-opto-mechanical actuation devices 142 based on feedback control loops between sensors 144 and the actuator devices/mechanisms 142. The present description is not intended to be an exhaustive list of all possible arrangements, but rather illustrate through an example, useful features in accordance with the present principles. Alternate embodiments, arrangements, configurations, etc. may also be employed and are contemplated.

Figure 4A:
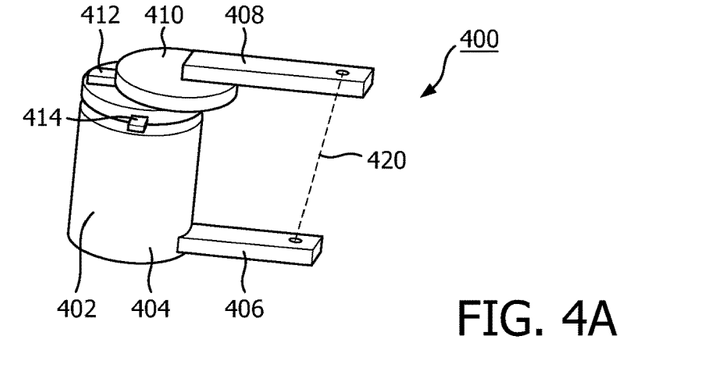
FIG. 4A is perspective view of a positioning and orientation apparatus in accordance with one embodiment.
Figure 4B:
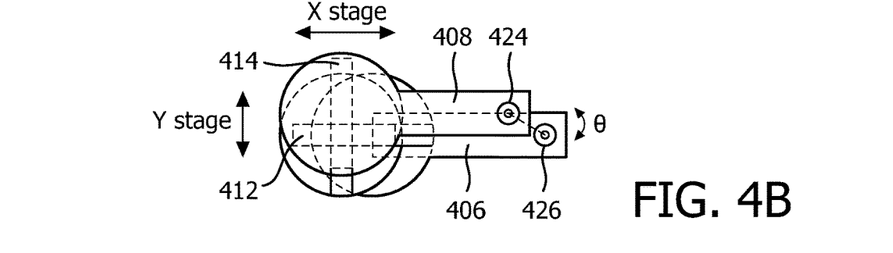
FIG. 4B is a top view of the apparatus of FIG. 4A.
Figure 4C:
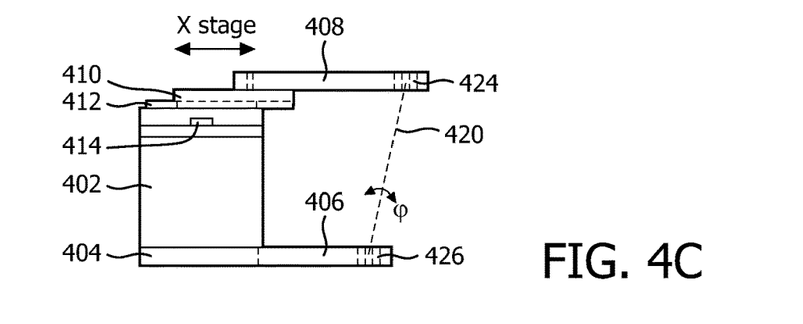
FIG. 4C is a side view of the apparatus of FIG. 4A.
Figure 4D:
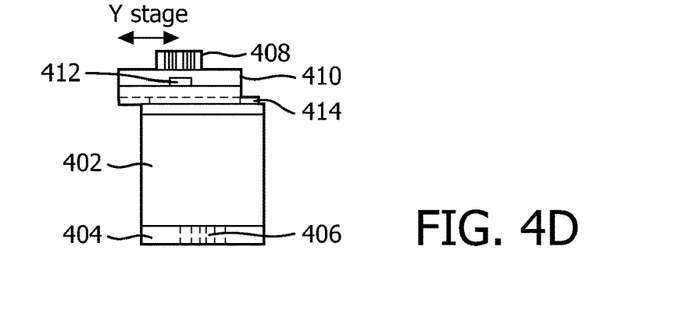
FIG. 4D is a back view of the apparatus of FIG. 4A.

Referring to FIGS. 4A-4D, a positioning and orientation apparatus 400 is shown for an endoscope port or other surgical device in accordance with one embodiment. FIG. 4A shows a perspective view of the apparatus 400. FIG. 4B shows a top view of the apparatus 400. FIG. 4C shows a side view of the apparatus 400. FIG. 4D shows a back view of the apparatus 400. The apparatus 400 includes two linear stages, an X stage 412 and a Y stage 414, connected to a cylindrical support 402. At a lower portion of the cylindrical support 402, a base 404 connects to a body of a subject or to a mounting mechanism (not shown) for such a purpose. Base 404 and a platform 410 each include a plate or beam 406 and 408, respectively, extending therefrom. Beam 408 maintains a fixed point of rotation around a port entry site opening 426 and provides a known spatial configuration relative to an endoscope view. Beam 408 holds a second point 424, which together with the fixed point of rotation of opening 426 of the beam 406 at the base 404 of the cylinder 402 defines an axis 420 through which a tool or needle can be inserted at a specific orientation into the port. The two points 424 and 426 are configured to hold a rigid hollow channel (e.g., a guide, etc.) through which the tool (not shown) may be inserted. Each of the two points 424 and 426 may include a spherical bearing to permit for correct tool positioning.

By changing the position of the two linear stages (X stage 412 and Y stage 414), the yaw and pitch angles (θ and φ) of the tool with respect to a point of rotation can be modified. The X and Y stages 412, 414 can be controlled manually using a lead screw with a manual lever, an encoder wheel or motion scale, or the stages 412, 414 can be controlled using a stepper or servo motor system with lead screws and encoders or potentiometers (see also FIG. 2 above).

Figure 5A:
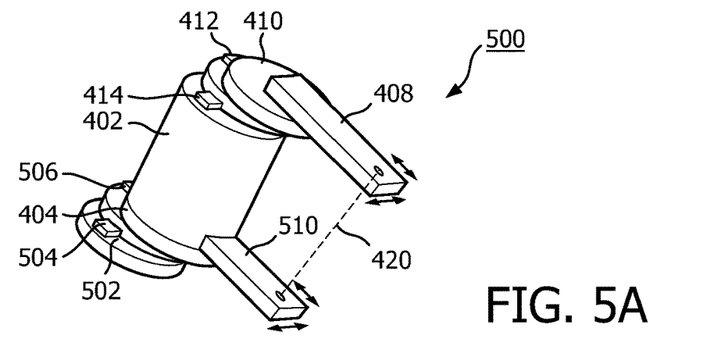
FIG. 5A is perspective view of another positioning and orientation apparatus in accordance with another embodiment.
Figure 5B:
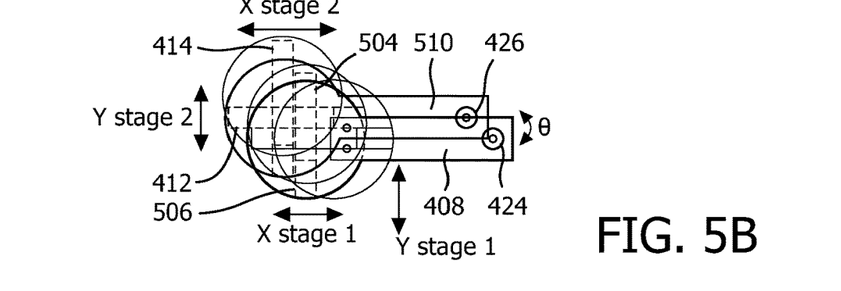
FIG. 5B is a top view of the apparatus of FIG. 5A.
Figure 5C:
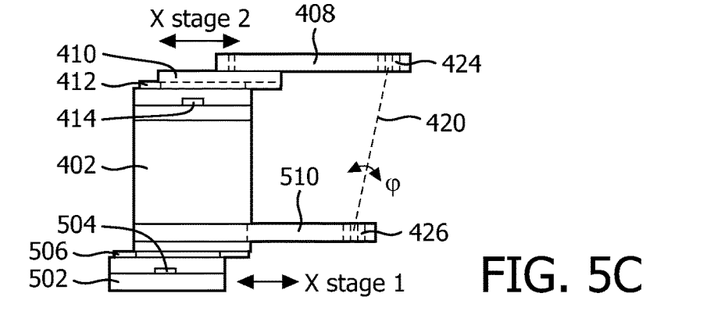
FIG. 5C is a side view of the apparatus of FIG. 5A.
Figure 5D:
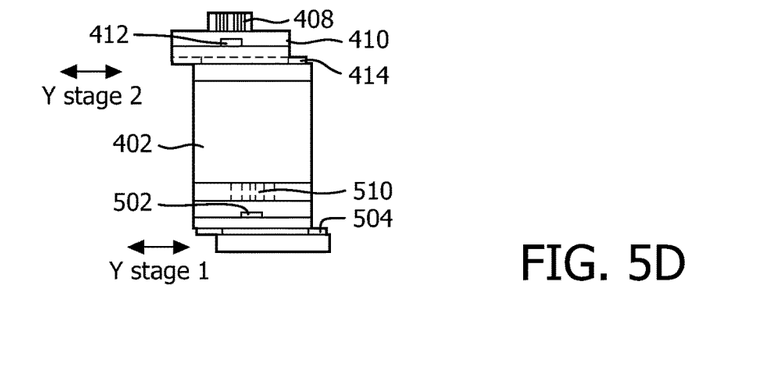
FIG. 5D is a back view of the apparatus of FIG. 5A.

Referring to FIGS. 5A-5D, a positioning and orientation apparatus 500 is shown for an endoscope port or other surgical device in accordance with another embodiment. FIG. 5A shows a perspective view of the apparatus 500. FIG. 5B shows a top view of the apparatus 500. FIG. 5C shows a side view of the apparatus 500. FIG. 5D shows a back view of the apparatus 500. The apparatus 500 includes four linear stages, an X stage 412 and a Y stage 414, connected at a top of the cylindrical support 402, and an X stage 506 and a Y stage 504 connected to a base 404 of the cylindrical support 402. At a lower portion of the cylindrical support 402, a base 502 connects to a body of a subject or to a mounting mechanism (not shown) for such a purpose.

At the bottom of the cylindrical support 402, a beam 510 maintains a fixed point 426 of rotation at a location of a port entry site. Two lower linear stages "X stage 1" 506 and "Y stage 1" 504 are located in a known position relative to the port access site. The linear stages at the top of the cylindrical support 402, "X stage 2" 412 and "Y stage 2" 414 are configured to change the yaw and pitch angles ($\theta$ and $\varphi$) of the tool with respect to a point of rotation. The XY stages can be controlled either manually using a lead screw with a manual lever in combination with an encoder wheel or motion scale (for feedback), or by using a stepper or servo motor system with lead screws, and encoders or potentiometers which form a (semi)automated feedback control loop, as described above. One advantage of including two sets of linear stages in this embodiment includes providing a capability for moving the "point of rotation" (X1, Y1) defined by the bottom linear stages 506, 504. This can be useful when aligning the tool with the port location.

Figure 6A:
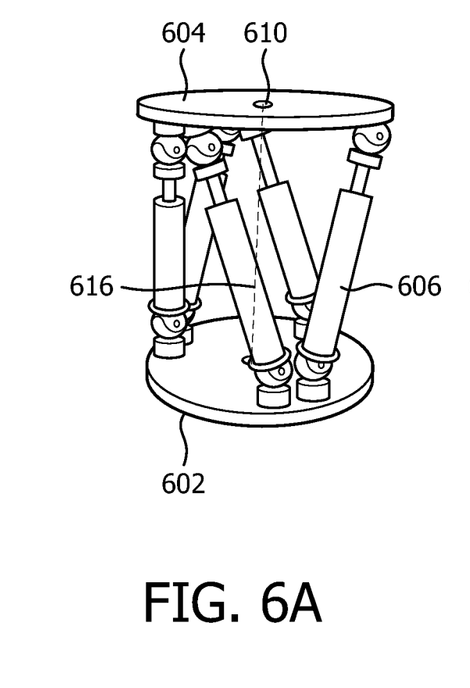
FIG. 6A is perspective view of yet another positioning and orientation apparatus in accordance with another embodiment.
Figure 6B:
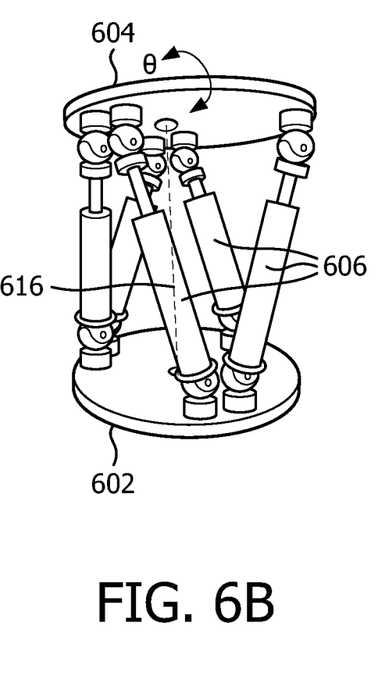
FIG. 6B is another perspective view showing a first rotation of a top plate of the apparatus of FIG. 6A.
Figure 6C:
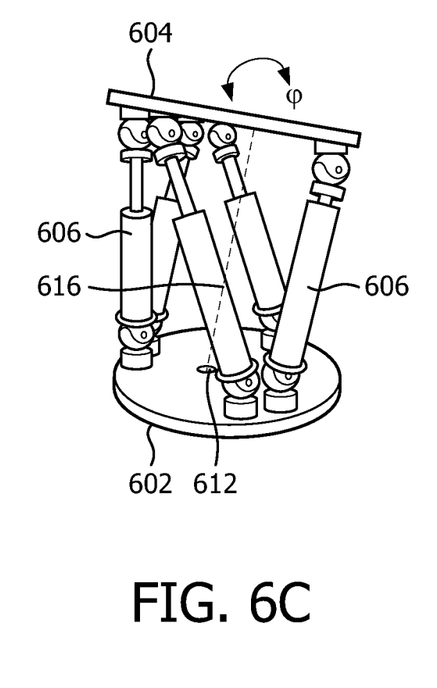
FIG. 6C is another perspective view showing a second rotation of a top plate of the apparatus of FIG. 6A.

Referring to FIGS. 6A-6C, another embodiment may include a Stewart platform assembly 600 which provides kinematics for a three degree of freedom (DOF) platform. Assembly 600 includes a base platform 602, which connects to a body of a subject or to a mounting mechanism (not shown) for being mounted on the subject. An upper platform 604 is coupled to the base platform 602 by a plurality of actuators 606, preferably linear actuators. The actuators 606 may be grouped in pairs and may have a "V" shaped configuration. The actuators 606 may be manually actuated, or the actuators 606 may include hydraulic or pneumatic cylinders, electromechanical mechanisms, etc. The actuators 606 may be controlled to provide rotation of a tool channel located between the platforms 602 and 604 and among the actuators 606. A portion of the base platform 604 may include a through-hole 610 at a center of rotation, which can be aligned with a port entry point. A similar portion of the upper platform 604 may include a through-hole 612 to permit the tool channel to pass. The holes 610 and 612 may have spherical joints to permit alignment in different configuration of the holes 610 and 612.

By moving the pairs of actuators 606 between platforms 602 and 604, the yaw and pitch angles ($\theta$ and $\varphi$) (FIGS. 6B and 6C, respectively) of a tool path 616 with respect to the center of rotation are modified. The actuators 606 can be moved using stepper or servo motors using position sensors (not shown). The actuators 606 may include simple lead screws which can be moved manually or under electro-optomechanical control, as long as there is some distance proprioception to assess the distance moved in each axis.

Figure 7A:
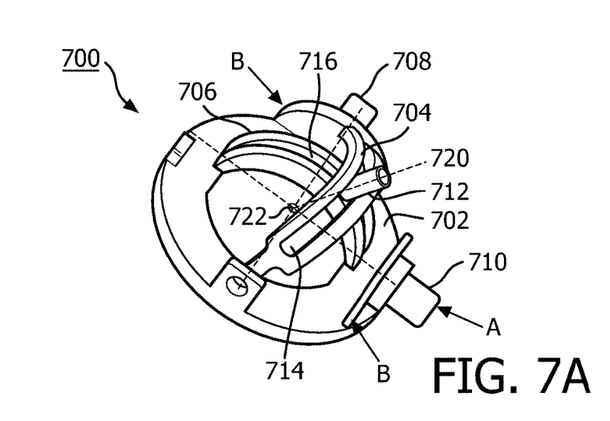
FIG. 7A is perspective view of still another positioning and orientation apparatus in accordance with another embodiment.
Figure 7B:
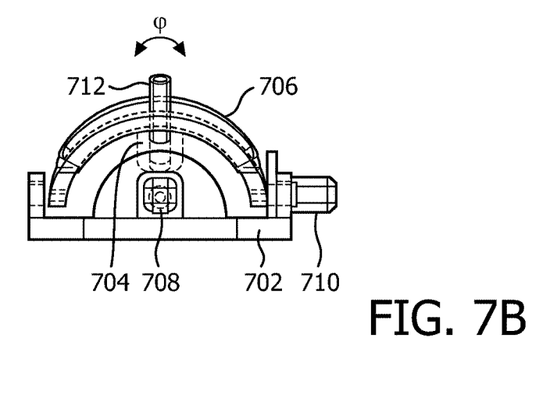
FIG. 7B is a top view of the apparatus of FIG. 7A.
Figure 7C:
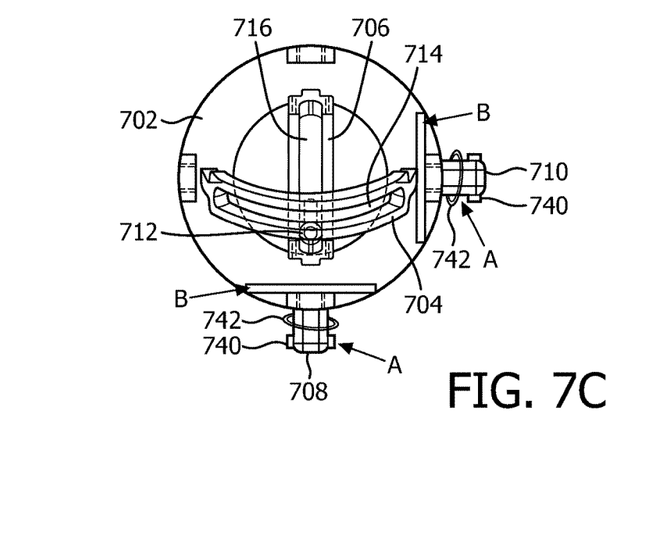
FIG. 7C is a side view of the apparatus of FIG. 7A.
Figure 7D:
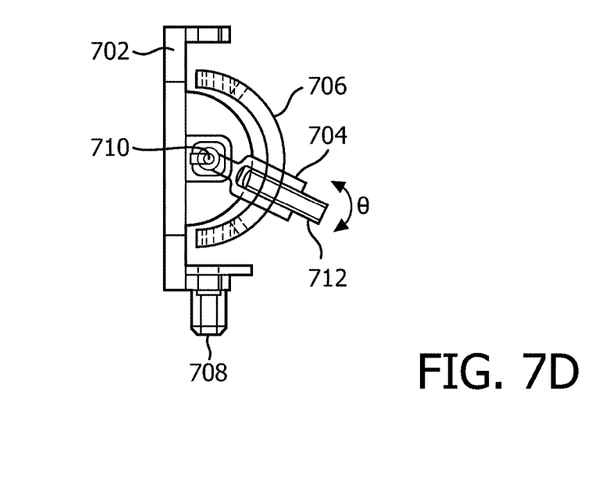
FIG. 7D is another side view of the apparatus of FIG. 7A.

Referring to FIGS. 7A-7D, a positioning and orientation apparatus 700 is shown for an endoscope port or other surgical device in accordance with another embodiment. FIG. 7A shows a perspective view of the apparatus 700. FIG. 7B shows a first side view of the apparatus 700. FIG. 7C shows a top view of the apparatus 700. FIG. 7D shows a second side view of the apparatus 700. The apparatus 700 includes two slotted arches 704 and 706, each having a centrally disposed slot 714 and 716, respectively. The arches 704 and 706 are hingedly connected to a base 702, which serves as a housing for hinge joints of axels 708 and 710. Axels 708 and 710 form hinged connections and are connected or integrally formed with their respective arches 704 and 706 to permit rotation of the arches 704 and 706 about the axels 708 and 710. The base 702 connects to a body of a subject or to a mounting mechanism (not shown) for conducting a procedure using the apparatus to position or orient a working channel for an endoscope or other instrument.

The arches 704, 706 provide a two axis system that can locate a tool axis 720 with two angular degrees of freedom (yaw and pitch—$\theta$ and $\varphi$) with respect to a center of rotation 722 located as close as possible to the port entry point. The center of rotation 722 is in alignment with a tube or channel (e.g., a guide) 712, and a tool axis 720 passes through the channel 712 and through the center of rotation to enter a subject through a port which is positioned at or around the center of rotation 722. The apparatus 700 may be attached to an endoscopy guidance system in a known geometry relative to the port entry site and imaging data stream.

The apparatus 700 may include many possible variations, examples of which will be described below in a non-exhaustive list. The apparatus 700 may provide manual motion of each of the two arches 704 and 706 to locate the tool (tool axis 720) at a desired angle. The apparatus 700 may provide manual motion of the two arches 704 and 706 to locate the tool (tool axis 720) and a brake 740 (shown in FIG. 7C only) may be located at points "A" to immobilize (e.g., prevent rotation) the arches 704 and 706, as needed. The apparatus 700 may include an encoder wheel 742 (shown in FIG. 7C only) without a sensor at points "B" to permit alignment of the arches 704, 706 to a scale marked on the encoder wheel 742, allowing direct visual feedback of the position of each arch. The apparatus 700 may include an optical encoder or potentiometer for each of the two axes corresponding to axels 708 and 710 at points "B". This can provide positional feedback for the position of each of the two arches 704 and 706 as an electrical (or optical) signal. The current position can be displayed on a screen or monitor (display 137) as well for reference.

The apparatus 700 may include combining an optical encoder (or potentiometer) system 742 with a light emitting diode (LED) display at points "B", where the LED display would indicate a desired position of each arch 704, 706 using a line or similar indicator. In this way, a user can manually or automatically set the positions of the arches 704, 706, and the optical encoder (or potentiometer) would show on a display 137 the current position of each of the arches 704, 706. The user could align the arch with the LED displayed line.

The apparatus 700 may include a stepper motor (not shown) at each of the points "A". This would permit motorized control of the tool positioning. The stepper motor at points "A" may be augmented with an optical encoder (or potentiometer) either located at points "B" or included in the stepper motor unit to provide positional feedback as well as motorized control. The apparatus 700 may include a servo motor system at each point "A", which may include a motor and optical encoder (or potentiometer) to provide motorized control of the tool positioning.

While the present embodiments have focused on controlling angular degrees of freedom, advancement and rotation of tools or tool channels is also contemplated. The advancement and rotation may also be performed manually, semi-automatically or automatically. The automatic advancement and rotation may include the use of motors, brakes, etc.

The present embodiments may be employed in many different applications, and are particularly useful for endoscopically-guided minimally invasive surgeries. For example, cardiac surgery, minimally invasive coronary artery bypass grafting, Atrial Septal Defect closure, valve repair/replacement, laparoscopic surgery, hysterectomy, prostatectomy, gall bladder surgery, Natural Orifice Transluminal Surgery (NOTES), pulmonary/bronchoscopic surgery, neurosurgical interventions, etc.

Figure 8:
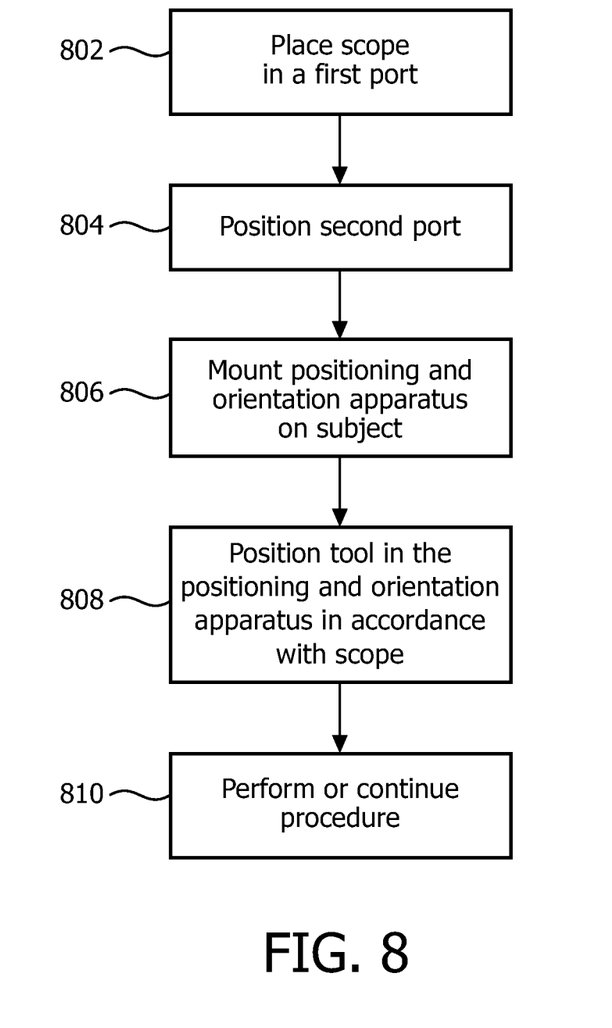
FIG. 8 is a block/flow diagram showing a method of positioning instruments in accordance with an illustrative embodiment.

Referring to FIG. 8, another method for positioning instruments is illustratively shown. In block 802, a scope (e.g., an endoscope) is placed in a first port in a subject. The scope port may be placed using port localization techniques including standard placement, patient specific placement, port optimization placement, etc. In block 804, a position for a second port for an instrument is determined. This preferably includes employing a port localization system to determine a mounting position on the subject for the positioning and orientation apparatus. Such a system uses patient specific data to select an optimal position for placement of the positioning and orientation apparatus.

In block 806, the positioning and orientation apparatus is mounted on the subject. The positioning and orientation apparatus includes two holes with adjustable positions for aligning a tool axis with respect to the second port. The positioning and orientation apparatus may include a first plate having a first opening for alignment with a port entry point, a second plate having a second opening for alignment with the first opening; and an actuation mechanism coupled to or between the first plate and the second plate and set to permit a tool axis to be aligned through the first and second openings such that a tool provided on the tool axis would pass through to a patient specific location in accordance with a plan. The positioning and orientation apparatus may include a first slotted arch hingedly coupled to a base, a second slotted arch hingedly coupled to the base and disposed orthogonally with respect to the first slotted arch and a channel disposed and passing through a slot in the first slotted arch and a slot of the second slotted arch for alignment of the channel with a center of rotation corresponding with a port entry point such that rotation of the tool axis is controlled by rotations of the first and second slotted arches to control alignment with a patient specific location in accordance with a plan. Other configurations may also be employed for the positioning and orientation apparatus, e.g., more than two plates or positioning points may be employed. This may include combinations of elements described herein or specially designed tools with or without adjustment mechanisms to support the positioning and orientation of instruments including endoscopes, surgical devices, needles, etc.

In block 808, a tool or tools are positioned along the tool axis through the two holes in accordance with a field of view of the scope. Multiple ports and multiple positioning and orientation apparatuses are contemplated. The tools are preferably maintained in the field of view of a camera or imaging device or in a predictable or known location to simplify user functions. The tool positioning and orientation may be controlled using feedback from a position and/or orientation of the scope. For example, the scope in the first port may be in a parallel plane with the instrument but skewed so that the instrument and the scope face each other. Alternately, the scope and the instrument may be parallel, both facing the same area of tissue. Other configurations are also contemplated. In block 810, a procedure is continued or performed using the instrument in a set position of the positioning and orientation apparatus. This set position may be adjusted or moved as needed (manually or automatically) before, during or after the procedure.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for positioning and orientation of surgical tools during patient specific port placement (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A positioning apparatus, comprising:
a first portion having a first opening for alignment with a port entry point;
a second portion being positionable for alignment with the first opening from a plurality of different positions relative to the first opening; and
an actuation mechanism coupled to the second portion and structurally configured to controllably set the second portion to one of the different positions relative to the first opening to permit a tool axis formed between the first and second portions to be aligned through the first opening such that a tool provided on the tool axis would include a known position and orientation.

2. The apparatus as recited in claim 1, wherein the actuation mechanism includes at least one stage for actuating the second portion relative to the first opening.

3. The apparatus as recited in claim 1, wherein the actuation mechanism includes two orthogonal stages for adjustment of the second portion relative to the first opening.

4. The apparatus as recited in claim 1, wherein the first opening is formed in a plate that is coupled to a base by a second actuation mechanism and the second actuation mechanism includes at least one stage for actuating the base relative to the plate.

5. The apparatus as recited in claim 1, wherein the actuation mechanism includes a plurality of piston-cylinder actuators.

6. The apparatus as recited in claim 1, wherein the first opening is formed in a plate that engages a mounting position on a subject such that the first opening corresponds with a port entry point in the subject.

7. The apparatus as recited in claim 6, further comprising a tool passing through the first opening and a second opening in the second portion and entering the entry port into the subject along the tool axis such that the tool is maintained in a visible position by a scope inside the subject.

8. The apparatus as recited in claim 7, wherein the actuation mechanism is computer controlled and set at a position based upon feedback from a position or view of the scope.

9. The apparatus as recited in claim 1, wherein the positioning apparatus is located on a subject by a port localization system.

10. A positioning apparatus, comprising:
a first plate having a first opening for alignment with a port entry point of a subject;

a second plate having a second opening for alignment with the first opening from a plurality of different positions relative to the first opening; and an actuation mechanism coupled to the second plate structurally configured to set the second plate to one of the different positions relative to the first opening to permit a tool axis to be aligned through the first and second openings such that a tool provided on the tool axis would pass through the port entry point with a known position and orientation.

11. The apparatus as recited in claim 10, wherein the actuation mechanism includes at least one stage for actuating the second portion relative to the first opening.

12. The apparatus as recited in claim 10, wherein the actuation mechanism includes two orthogonal stages for adjustment of the second portion relative to the first opening.

13. The apparatus as recited in claim 10, wherein the first opening is formed in a plate that is coupled to a base by a second actuation mechanism and the second actuation mechanism includes at least one stage for actuating the base relative to the plate.

14. The apparatus as recited in claim 10, wherein the actuation mechanism includes a plurality of piston-cylinder actuators.

15. The apparatus as recited in claim 10, wherein the first opening is formed in a plate that engages a mounting position on the subject such that the first opening corresponds with a port entry point in the subject.

16. The apparatus as recited in claim 15, further comprising a tool passing through the first opening and a second opening in the second portion and entering the entry port into the subject along the tool axis such that the tool is maintained in a visible position by a scope inside the subject.

17. The apparatus as recited in claim 16, wherein the actuation mechanism is computer controlled and set at a position based upon feedback from a position or view of the scope.

18. The apparatus as recited in claim 10, wherein the positioning apparatus is located on a subject by a port localization system.

19. A method for positioning instruments, comprising:

placing a scope in a first port in a subject;

determining a position for a second port for an instrument;

mounting a positioning and orientation apparatus to the subject; the positioning and orientation apparatus including a first opening and a second opening, for aligning a tool axis with respect to the second port;

operating the position and orientation apparatus to controllably set the second opening to one of a plurality of different positions relative to the first opening; and positioning a tool along the tool axis through the first opening and the second opening in accordance with a field of view of the scope.

* * * * *